United States Patent
Krivoruchko et al.

(10) Patent No.: US 9,056,351 B2
(45) Date of Patent: Jun. 16, 2015

(54) STENT WITH IMPROVED FLEXIBILITY AND METHOD FOR MAKING SAME

(71) Applicant: Medtronic Vascular, Inc., Santa Rosa, CA (US)

(72) Inventors: Michael Krivoruchko, Forestville, CA (US); Joseph Lessar, Mora, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 254 days.

(21) Appl. No.: 13/759,334

(22) Filed: Feb. 5, 2013

(65) Prior Publication Data

US 2013/0146173 A1 Jun. 13, 2013

Related U.S. Application Data

(62) Division of application No. 11/624,343, filed on Jan. 18, 2007, now abandoned.

(51) Int. Cl.
*A61F 2/90* (2013.01)
*B21F 99/00* (2009.01)
*C21D 7/04* (2006.01)

(52) U.S. Cl.
CPC .................. *B21F 99/00* (2013.01); *Y10T 29/49* (2015.01); *A61F 2/90* (2013.01); *A61F 2250/0029* (2013.01); *C21D 7/04* (2013.01); *C21D 2201/01* (2013.01); *A61F 2230/0054* (2013.01)

(58) Field of Classification Search
CPC ........... A61F 2/82–2/945; B21F 99/00; Y10T 29/49968
USPC ........................................................ 29/525.14
See application file for complete search history.

(56) References Cited

U.S. PATENT DOCUMENTS

| | | | | |
|---|---|---|---|---|
| 5,104,404 A | * | 4/1992 | Wolff | 623/1.16 |
| 5,817,152 A | | 10/1998 | Birdsall et al. | |
| 5,843,175 A | * | 12/1998 | Frantzen | 623/1.15 |
| 6,099,559 A | * | 8/2000 | Nolting | 623/1.16 |
| 6,136,023 A | | 10/2000 | Boyle | |
| 6,231,698 B1 | | 5/2001 | Braunheim et al. | |
| 6,331,189 B1 | * | 12/2001 | Wolinsky et al. | 623/1.15 |
| 6,547,818 B1 | * | 4/2003 | Rourke et al. | 623/1.16 |
| 6,635,083 B1 | | 10/2003 | Cheng et al. | |
| 7,060,090 B2 | | 6/2006 | Thornton | |
| 2004/0127970 A1 | | 7/2004 | Saunders et al. | |
| 2005/0055080 A1 | | 3/2005 | Istephanous et al. | |
| 2005/0256563 A1 | | 11/2005 | Clerc et al. | |

(Continued)

FOREIGN PATENT DOCUMENTS

| | | |
|---|---|---|
| EP | 1579824 | 9/2005 |
| WO | WO2005/067816 | 7/2005 |
| WO | WO 2005067816 A1 * | 7/2005 |

*Primary Examiner* — Jacob Cigna

(57) ABSTRACT

A stent and a method for manufacturing a stent are provided. The stent includes a first ring having a plurality of peaks and a plurality of valleys, a second ring having a plurality of peaks and a plurality of valleys, and a connector that connects one of the peaks of the first ring to one of the valleys of the second ring. The connected peak of the first ring includes a deformed portion that extends towards the connected valley of the second ring. The method includes forming a first ring having a plurality of peaks and a plurality of valleys, forming a second ring having a plurality of peaks and a plurality of valleys, deforming a portion of at least one of the peaks of the first ring, and connecting the deformed portion of the peak of the first ring to one of the valleys of the second ring.

18 Claims, 4 Drawing Sheets

(56) References Cited

U.S. PATENT DOCUMENTS

| | | |
|---|---|---|
| 2006/0136037 A1 | 6/2006 | DeBeer et al. |
| 2006/0247758 A1 | 11/2006 | Krivoruchko |
| 2007/0168010 A1* | 7/2007 | Goshgarian ................. 623/1.11 |
| 2008/0177376 A1* | 7/2008 | Krivoruchko et al. ....... 623/1.16 |
| 2008/0262628 A1* | 10/2008 | Laitenberger et al. ....... 623/23.7 |
| 2013/0282107 A1* | 10/2013 | Baldwin et al. .............. 623/1.22 |

* cited by examiner

STENT WITH IMPROVED FLEXIBILITY AND METHOD FOR MAKING SAME

RELATED APPLICATIONS

This application is a Division of and claims the benefit of U.S. patent application Ser. No. 11/624,343 filed Jan. 18, 2007, now abandoned.

BACKGROUND OF THE INVENTION

1. Field of the Invention

The present invention relates generally to a stent with improved flexibility. More specifically, the present invention relates to a welded stent having increased flexibility at the welded connections.

2. Description of Related Art

A stent is a prosthesis that is inserted into a body lumen and used, for example, for treating stenoses, strictures, and/or aneurysms therein. In the event of a stenosed vessel, a stent may be used to prop open the vessel after an angioplasty procedure. Once opened, the stent forms to the inner wall of the vessel, remains in place, and may help prevent restenosis. Additionally, in the event of an aneurysm or weakened vessel wall, stents may be used to provide support to, and reinforce the vessel wall.

To perform such functions, stents in the past have included many different structures. For example, previously disclosed stents include coiled stainless steel springs, helical wound springs, and generally serpentine configurations with continuous waves of generally sinusoidal character. Some of these stents self deploy when placed in the vessel, whereby stent expansion is primarily achieved by removing a restraint mechanism holding the stent in a constricted state. Other types of stents rely on alternate means to deploy, for example, use of a balloon catheter system, whereby balloon dilation expands and deploys the stent.

One of the major complications associated with using stents has been thrombosis. This complication is caused by clotting in the vicinity of the stent and is associated with high morbidity and mortality. It has been shown that the better the stent apposition against the vessel wall and the larger the lumen, the less likely that this complication will occur. A further complication is restenosis, which is caused by tissue proliferation around the angioplasty site. To minimize the potential for restenosis, the stent should cover the lesion and not leave any significant gaps in which restenosis may occur. The stent should also adhere to the inner wall of the vessel as much as possible.

Accordingly, when a stent deploys in a restricted vessel, adequate radial strength is required to overcome the strictures and ensure apposition of the stent to the vessel wall. Radial strength is a force produced by the stent acting at all points on the vessel wall in an outwardly direction perpendicular to the vessel wall. Stents are designed with circumferential rings to provide most of the radial strength needed to overcome radial forces pushing inwardly against the stent as the stent expands.

Many stents also include longitudinal links that primarily act to attach longitudinally adjacent circumferential rings, but also add radial strength and stent stability. Once the stent is fully deployed, in addition to providing adequate radial strength, the stent must provide adequate vessel wall coverage, hereinafter referred to as scaffolding affect. Scaffolding affect is defined as the amount of area of the vessel wall covered by the stent, once the stent is fully deployed. The circumferential rings and longitudinal links connecting the circumferential rings have traditionally provided the needed scaffolding affect. Other stents include welded connections between longitudinally adjacent circumferential rings.

Further, to meet the demands of adequate radial strength and scaffolding affect, conventional stents have been designed with circumferential rings manufactured with adequate ring width, which were then continuously connected at each peak and valley or trough by longitudinal links. However, such conventional stents suffer from predilation stent longitudinal rigidity. Predilation or crimped stent longitudinal rigidity is a resistance to movement and decreased flexibility of the stent along the stent's longitudinal axis. Accordingly, predilation longitudinal stent rigidity makes it much harder and oftentimes even impossible to thread the stent through long tortuous vessels and past constrictions and lesions.

Past attempts have been made to overcome predilation stent longitudinal rigidity. Such attempts have included designs with decreased ring width, often referred to as decreased wire gauge, which resulted in increased longitudinal flexibility but decreased radial strength. These conventional designs have resulted in inadequate stent apposition and/or inadequate vessel wall support. Additionally, past attempts to increase longitudinal flexibility have included designs where longitudinal links are not attached to each peak and valley of the circumferential ring. Thus, only some of the peaks and valleys of adjacent circumferential rings are connected by longitudinal links. This increases longitudinal flexibility but decreases the scaffolding affect of the stent. The decreased scaffolding affect creates areas where the vessel wall is not adequately covered by the stent, which may lead to thrombosis and/or restenosis.

Additionally, in order to meet the requirements of drug eluting stents, conventional stent substrates have been designed with circumferential elements manufactured with adequate ring/strut/apex width, which were then continuously connected at each peak and valley by longitudinal links. However, such conventional stents may suffer from abrasion or damage due to adjacent apexes (i.e., peaks and valleys) interacting during crimping and tracking, which may be caused by the close proximity of adjacent apexes coming into contact with one another due to links or weld not providing adequate clearance. This interaction may cause abrasion or damage during the coating of the stent with a drug and/or polymer or during tracking of the stent through the anatomy.

Accordingly, there arises the need for a stent, which provides adequate radial strength, scaffolding affect, with increased apex spacing and longitudinal flexibility. It is among the objects of the present invention to provide a stent that overcomes the foregoing shortcomings and meets the needs discussed above.

SUMMARY OF THE INVENTION

One aspect of the present invention provides a stent having improved longitudinal flexibility and minimal apex to apex (i.e., peak to valley) interaction between adjacent rings.

In an embodiment of the present invention, a stent is provided. The stent includes a first ring having a plurality of peaks and a plurality of valleys, a second ring having a plurality of peaks and a plurality of valleys, and a connector connecting one of the peaks of the first ring to one of the valleys of the second ring. The connected peak of the first ring includes a deformed portion that extends towards the connected valley of the second ring.

Another aspect of the present invention provides a method for manufacturing a stent with improved longitudinal flexibility and increased apex to apex spacing between adjacent rings.

In an embodiment of the present invention, a method for manufacturing a stent is provided. The method includes forming a first ring having a plurality of peaks and a plurality of valleys, forming a second ring having a plurality of peaks and a plurality of valleys, deforming a portion of at least one of the peaks of the first ring, and connecting the deformed portion to one of the valleys of the second ring.

In another embodiment of the present invention, a method for manufacturing a stent is provided. The method includes forming a first ring having a plurality of peaks and a plurality of valleys, forming a second ring having a plurality of peaks and a plurality of valleys, connecting one of the peaks of the first ring to one of the valleys of the second ring, and deforming a portion of the connected peak of the first ring.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

Embodiments of the present invention will now be described, by way of example only, with reference to the accompanying schematic drawings in which corresponding reference symbols indicate corresponding parts, and in which.

DETAILED DESCRIPTION OF EMBODIMENTS OF THE INVENTION

The foregoing and other features and advantages of the invention will be apparent from the following, more detailed description of the preferred embodiment of the invention, as illustrated with reference to the Figures. While specific embodiments are discussed in detail, it should be understood that this is done for illustrative purposes only. A person skilled in the art will recognize that other embodiments can be used without departing from the spirit and scope of the invention.

Figure 1:
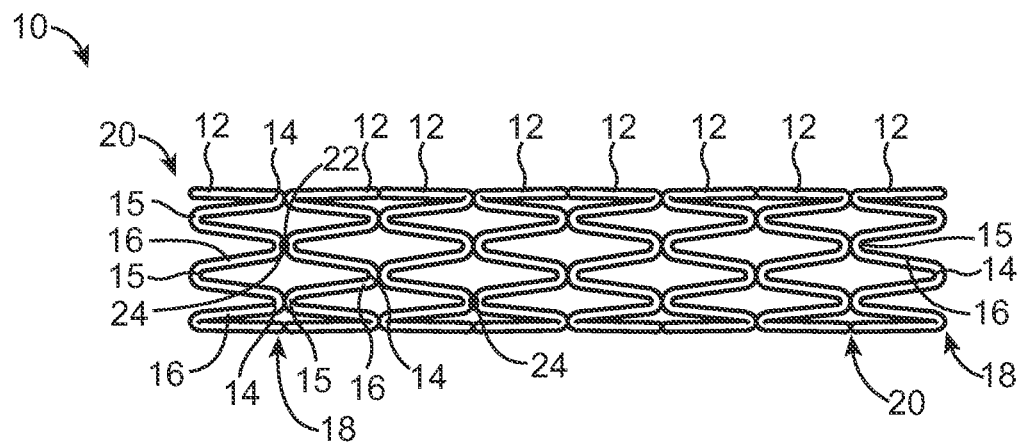
FIG. 1 illustrates a stent in accordance with an embodiment of the invention.

FIG. 1 illustrates a stent 10 according to an embodiment of the invention. As illustrated, the stent 10 includes a plurality of circumferential rings 12 that are each in the shape of a sinusoid. Each ring 12 includes a plurality of peaks 14 and a plurality of valleys 15 that are connected to each other by a plurality of segments 16. A proximal end 18 of the sinusoid has been arbitrarily labeled "peak" and a distal end 20 of the sinusoid has been arbitrarily labeled "valley." It would be understood by one of ordinary skill in the art that the peaks 14 and valleys 15 have been labeled for illustrative purposes and ease of understanding and that the terms may be switched.

Each ring 12 may be formed from a single piece of material, such as a metal wire, or each ring/element 12 may be cut from a metal tube. For rings 12 that are formed from a single wire, the ends of the wire may be welded together so as to form a continuous ring. The material used to fabricate the rings 12 can be made of an inert, biocompatible material with high corrosion resistance that can be plastically deformed at low-moderate stress levels such as tantalum, or moderate to high stress levels such as L605, MP35N, or any other high work hardening rate material. Other acceptable materials include, but are not limited to, nickel titanium, stainless steel, titanium ASTM F63-83 Grade 1, niobium, cobalt-chromium (Co—Cr) alloys, and other cobalt-based alloys. A self-expanding device can be made by the use of superelastic NiTi, such as nitinol. As discussed in further detail below, a single ring may be connected to an adjacent ring with a connector 22, such as a weld 24, so as to form a flexible connection between the rings.

Figure 2:
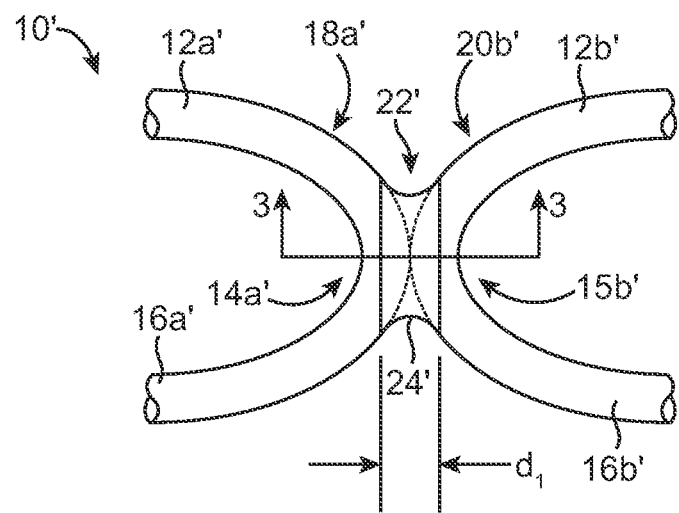
FIG. 2 illustrates a detailed view of a connection between two adjacent rings of a conventional welded stent.
Figure 3:
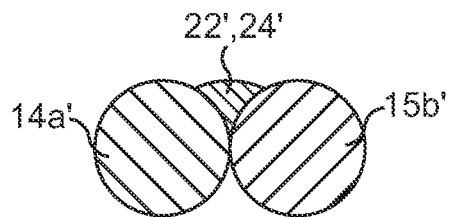
FIG. 3 is a cross-sectional view taken along line 3-3 in FIG. 2.

FIGS. 2 and 3 illustrate a conventional connection between adjacent rings 12a', 12b' of a stent 10'. As illustrated, the rings 12a', 12b' may be connected with a connector 22'. In the illustrated embodiment, the connector 22' is a weld 24'. During the manufacturing process, the adjacent rings 12a', 12b' are placed in contact with each other so that a peak 14a' of one ring 12a' contacts a valley 15b' of an adjacent ring 12b'. The weld 24' is then created at the contact point of the peak 14a' and valley 15b' so as to form the connector 22'. The weld 24' may be created by conventional welding techniques, including but not limited to butt welding, resistance welding, and/or laser welding. As shown in FIG. 2, the resulting weld 24' has a length of $d_1$. Such a configuration may provide a connection with limited flexibility, because the peak 14a' and valley 15b' are abutted against each other, and the length $d_1$ of the weld 24' is relatively short. In order to increase the length of the weld, the peaks 14a' and the valley 15b' of the adjacent rings 12a', 12b' would have to be spaced further apart before the weld 24' is created, which may lead to inconsistent weld lengths and/or weaker connections.

Figure 4:
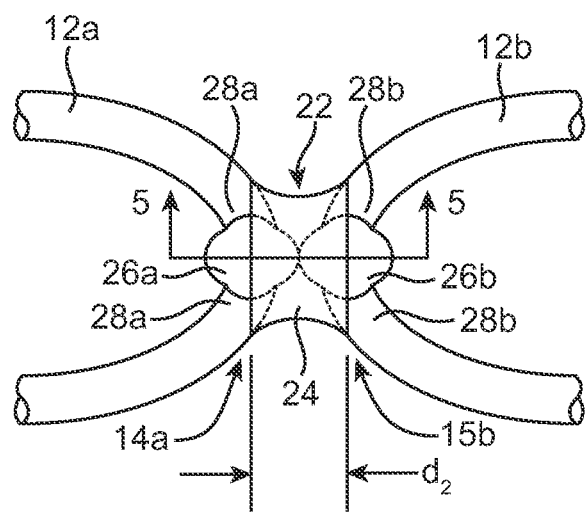
FIG. 4 illustrates a detailed view of a connection between two adjacent rings of a stent according to an embodiment of the invention.
Figure 5:
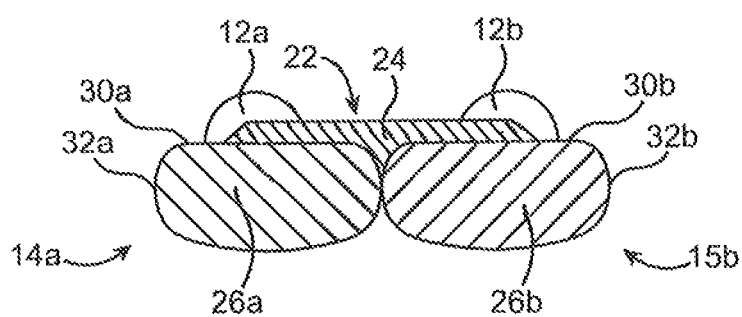
FIG. 5 is a cross-sectional view taken along line 5-5 in FIG. 4.

FIGS. 4 and 5 illustrate a connection between adjacent rings 12a, 12b according to an embodiment of the invention. As illustrated, a peak 14a of one of the rings 12a includes a deformed portion 26a and non-deformed portions 28a that are on opposite sides of the deformed portion 26a. Similarly, a valley 15b of the adjacent ring 12b includes a deformed portion 26b and non-deformed portions 28b that are on opposite sides of the deformed portion 26b. The deformed portions 26a, 26b may be created by methods discussed in further detail below. In the illustrated embodiment, the rings 12a, 12b are connected with a connector 22 in the form of a weld 24.

Figure 6:
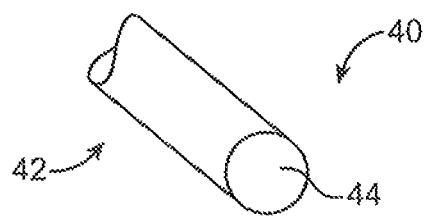
FIG. 6 is a perspective view of a distal end of an embodiment of a tool used to manufacture the stent of FIG. 1.

As shown in greater detail in FIG. 5, the deformed portions 26a, 26b each include a recess 30a, 30b, respectively, that are recessed from the respective non-deformed portions 28a, 28b of the peak 14a and the valley 15b, respectively. As discussed in further detail below, as each recess 30a, 30b is created, at least one extension 32a, 32b, respectively, is also created, due to the displacement of the material. In an embodiment, one of the extensions 32a of the recess 30a extends in a direction that is toward the valley 15b of the adjacent ring 12b, as shown in FIG. 6, and the other extension 32a extends in a direction that is away from the valley 15b of the adjacent ring 12b. Although two extensions 32a are illustrated, in some embodiments, the recess 30a may only include a single extension that extends towards the valley 15b of the adjacent ring 12b. The illustrated embodiment is not intended to be limiting in any way.

As discussed in further detail below, the deformed portions 26a, 26b may be created by work hardening (e.g., cold-working) the material in the peak 14a and the valley 15b, respectively, such that the material plastically deforms, thereby creating the recesses 30a, 30b and the extensions 32a, 32b. As a result of work hardening the material, the deformed portions 26a, 26b may have a hardness that is greater than the hardness of the non-deformed portions 28a, 28b of the peak 14a and the valley 15b, respectively.

In an embodiment, the material in the deformed portions 26a, 26b have a hardness that is at least about 20%, and preferably between about 20% and about 40%, higher than the hardness of the material in the non-deformed portions 28a, 28b due to the work hardening of the material. For example, in an embodiment, the ring 12a may be made from annealed stainless steel, or Co—Cr alloy having a Vickers hardness of about 220 HV, while the hardness of the material of the deformed portion 26a that has been work-hardened may be about 300 HV, which is an increase of about 36%.

Of course, the actual amount of increase in hardness of the material in the deformed portion 26a will depend on the material, the degree of deformation, the working temperature, and the amount and duration of pressure that is applied to the material. The same considerations apply to the deformation of the valley 15b of the adjacent ring 12b, if applicable. In some embodiments, only the peak of one ring is deformed and is connected to a non-deformed valley of an adjacent ring. The illustrated embodiment is not intended to be limiting in any way.

By creating the deformed portions 26a, 26b in the peak 14a and the valley 15b, respectively, by work hardening the material, not only are the extensions 32a, 32b created, but the strength of the extensions 32a, 32b may be increased. This may allow the connection between the peak 14a and the valley 15b to be more flexible, yet stronger. Increased flexibility may be achieved by allowing the non-deformed portions 28a, 28b of the peak 14a and the valley 15b in the adjacent rings 12a, 12b, respectively, to be spaced apart at a greater distance than other connected peaks and valleys, such as the peak 14a' and valley 15b' illustrated in FIGS. 2 and 3 and discussed above.

For example, as discussed above, in the conventional welded stent 10', the weld 24' has a length of $d_1$. However, in the embodiment illustrated in FIG. 4, the weld 24 of the stent 10 has a length $d_2$, which is greater than $d_1$ due to the presence of the extensions 32a, 32b of the deformed portions 26a, 26b of the peak 14a, and the valley 15b, respectively. The longer weld 24 (as compared to the weld 24' illustrated in FIGS. 2 and 3) may improve the flexibility of the connector 22, while the work hardened material in the deformed portions 26a, 26b may increase the strength of the connector 22. In other words, the presence of the extensions 32a, 32b within the weld 24 may increase the strength of the connection between the adjacent rings 12a, 12b, and at the same time provide a more flexible connection.

The weld 24 may be created by conventional welding techniques, including but not limited to butt welding, resistance welding, and/or laser welding. In addition, it is contemplated that the connector 22 may not be in the form of a weld per say, and may be created by soldering or brazing.

In an embodiment, heat may be generated at the peak 14a and the valley 15b with a laser, so as to cause the material in the peak 14a and the valley 15b to flow together, thereby creating the weld 24. As the weld 24 is created, an inert gas, such as argon or helium, may be used to flood the weld area at a sufficient flow rate to prevent oxidation so that the weld 24 does not become brittle. Of course, other welding techniques may be used, and the above-described method should not be considered to be limiting in any way.

FIG. 6 shows an embodiment of a tool 40 that may be used to create the deformed portion 26a of the peak 14a of the ring 12a described above. Of course, the same tool 40 may be used to create the deformed portion 26b of the valley 15b of the ring 12b as well. The tool 40 is preferably fabricated from a material having a greater hardness than the material used to form the ring 12a. In the embodiment illustrated in FIG. 6, the tool 40 includes a punch 42 that has a circular cross-section and a distal end 44 that is flat. Of course, the punch 42 may have other cross-sectional shapes, such as ellipsoid, rectangular, etc. The illustrated embodiment of the punch 42 is not intended to be limiting in any way.

Figure 7:
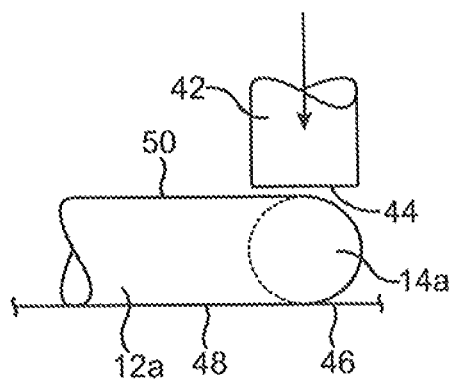
FIG. 7 is a side view of the tool of FIG. 6 just before it is applied to one of the rings of FIG. 4 in accordance with an embodiment of the invention.
Figure 8:
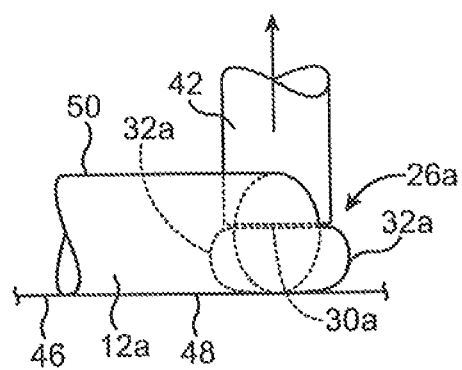
FIG. 8 is a side view of the tool of FIG. 6 just after it has been applied to the ring of FIG. 7.

A support 46 may be placed inside the ring 12 so that it contacts an inside surface 48 of the peak 14a, as shown in FIG. 7. The support 46 may be a mandrel, or any other structure that is configured to support the ring 12a as the punch 42 is used to create the deformed portion 26a of the peak 14a. After the ring 12a has been properly positioned on the support 46, the punch 42 may engage an outside surface 50 of the peak 14a at a location of the peak 14a where the deformed portion 26a should be created. With the peak 14a positioned between the support 46 and the punch 42, suitable pressure may be applied to the punch 42 until the desired amount of deformation takes place, as shown in FIG. 8. The suitable pressure should be enough pressure to cause the material of the peak 14a to flow, yet not too great to cause the material at the peak 14a to fracture. As would be appreciated by one of ordinary skill in the art, the stress-strain curve of the material used to form the rings 12 may be used to select the suitable pressure. After the desired amount of deformation has taken place, the punch 42 may be removed from the peak 14a, thereby leaving the deformed portion 26a behind.

Figure 9:
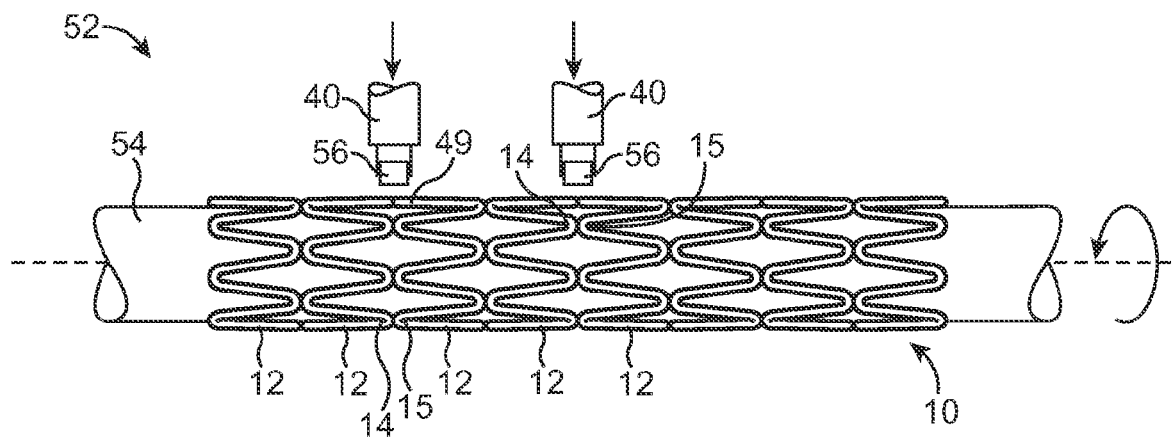
FIG. 9 is a side view of a portion of an apparatus used to manufacturing the stent of FIG. 1 according to another embodiment of the invention.
Figure 10:
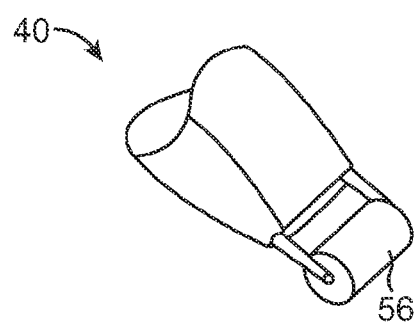
FIG. 10 is a perspective view of a distal end of a tool of the apparatus of FIG. 9.

In another embodiment, the deformed portions 26 a, 26 b may be formed simultaneously by using an apparatus 52 illustrated in FIG. 9. As illustrated, the apparatus 52 includes a mandrel 54 on which the rings 12 of the stent 10 are placed. The apparatus 52 also includes a plurality of tools 40 that are aligned along the mandrel 54 such that the tools 40 are axially aligned with the peaks 14 of the rings 12. In an embodiment, illustrated in greater detail in FIG. 10, the tool 40 includes a roller 56 at a distal end thereof. The mandrel 54 may be rotated and the tools 40 may be moved towards the mandrel so that each roller 56 may engage the outer surfaces 49 of the peaks 14. As shown, a single roller 56 may engage a peak 14 of one ring and a valley 15 of an adjacent ring 12 at the same time. Of course, other arrangements may be used. For example, if deformed portions 26 are to be created in only certain peaks 14 and/or valleys 15, rather than all of the peaks 14 and valley 15, the mandrel 54 and the rollers 56 may be indexed so that the rollers 56 only contact the peaks 14 in which the deformed portions 26 are to be created. The illustrated embodiment is not intended to be limiting in any way.

In another embodiment, that peak 14a and the valley 15b of adjacent rings 12a, 12b may first be welded together, as shown in FIG. 2, and the tool 40 (either with the punch 48 of FIG. 6 or the roller 56 of FIG. 10) may then be used to create the deformed portions 26a, 26b of the peak 14a and the valley 15b, respectively, in the manner discussed above. Both methods are contemplated as being within embodiments of the present invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A method for manufacturing a stent, the method comprising: forming a first continuous wire into a first circumferential ring having an outer surface facing away from a longitudinal axis and having a sinusoidal shape defined by a plurality of peaks connected to a plurality of valleys by a plurality of segments; forming a second continuous wire into a second circumferential ring having an outer surface facing away from a longitudinal axis and having a sinusoidal shape defined by a plurality of peaks connected to a plurality of valleys by a plurality of segments; deforming a peak of the first ring such that a deformed peak portion is unitary with and flanked by non-deformed peak portions on opposite sides, the deformed peak portion having i) an outer surface recessed below outer surfaces of the flanking non-deformed peak portions, and ii) an extension that protrudes in a longitudinal direction away from the first ring and consists of displaced material of the first continuous wire; and abutting and connecting the extension of the deformed peak portion to a valley of the second ring so as to space the non-deformed peak portions from the valley; wherein said connecting comprises welding.

2. The method according to claim 1, wherein said deforming comprises work hardening the deformed peak portion.

3. The method according to claim 2, wherein the Vickers hardness value of the deformed peak portion increases by at least about 20% during said work hardening.

4. The method according to claim 3, wherein the Vickers hardness value of the deformed peak portion increases by about 20% to about 40% during said work hardening.

5. The method according to claim 1, further comprising deforming a valley of the second ring such that a deformed valley portion is unitary with and flanked by non-deformed valley portions on opposite sides, the deformed valley portion having i) an outer surface recessed below outer surfaces of the flanking non-deformed valley portions, and ii) an extension that protrudes in a longitudinal direction away from the second ring and consists of displaced material of the second continuous wire, and wherein said connecting and abutting step comprises connecting and abutting the extension of the deformed peak portion of the first ring to the extension of the deformed valley portion of the second ring so as to space the non-deformed peak portions from the non-deformed valley portions.

6. The method according to claim 5, wherein said deforming the valley of the second ring comprises work hardening the deformed portion of the valley.

7. The method according to claim 6, wherein the Vickers hardness value of the deformed valley portion of the second ring increases by at least about 20% during said work hardening.

8. The method according to claim 7, wherein the Vickers hardness value of the deformed valley portion of the second ring increases by about 20% to about 40% during said work hardening.

9. The method according to claim 1, wherein said deforming comprises pressing a tool against the peak portion.

10. The method according to claim 9, wherein the tool comprises a punch.

11. The method according to claim 9, wherein the tool comprises a roller.

12. A method for manufacturing a stent, the method comprising: forming a first continuous wire into a first circumferential ring having an outer surface facing away from a longitudinal axis and having a sinusoidal shape defined by a plurality of peaks connected to a plurality of valleys by a plurality of segments; forming a second continuous wire into a second circumferential ring having an outer surface facing away from a longitudinal axis and having a sinusoidal shape defined by a plurality of peaks connected to a plurality of valleys by a plurality of segments; connecting a peak of the first ring to a valley of the second ring; and following connection of the peak and the valley, deforming the connected peak and valley such that: a deformed peak portion is unitary with and flanked by non-deformed peak portions on opposite sides, the deformed peak portion having i) an outer surface recessed below outer surfaces of the flanking non-deformed peak portions, and ii) an extension consisting of displaced material of the first continuous wire; and a deformed valley portion is unitary with and flanked by non-deformed valley portions on opposite sides, the deformed valley portion having i) an outer surface recessed below outer surfaces of the flanking non-deformed valley portions, and ii) an extension consisting of displaced material of the second continuous wire; wherein the extension of the deformed peak portion protrudes from the peak into abutment with the extension of the deformed valley portion protruding from the valley so as to space the non-deformed peak portions from the non-deformed valley portions; wherein said connecting step comprises one of butt welding, resistance welding, laser welding, brazing or soldering.

13. The method according to claim 12, wherein said deforming comprises work hardening.

14. The method according to claim 13, wherein the Vickers hardness value of the deformed peak portion increases by at least about 20% during said work hardening.

15. The method according to claim 14, wherein the Vickers hardness value of the deformed peak portion increases by about 20% to about 40% during said work hardening.

16. The method according to claim 12, wherein said deforming step comprises pressing a tool against the connected peak and valley.

17. The method according to claim 16, wherein the tool comprises a punch.

18. The method according to claim 16, wherein the tool comprises a roller.

* * * * *